(12) United States Patent
Agarwal

(10) Patent No.: US 10,631,794 B2
(45) Date of Patent: Apr. 28, 2020

(54) DEVICE FOR EXTERNALLY MARKING THE LOCATION OF ORGANS ON SKIN DURING A CAT SCAN

(71) Applicant: Ghansham Das Agarwal, Shahjahanpur (IN)

(72) Inventor: Ghansham Das Agarwal, Shahjahanpur (IN)

( * ) Notice: Subject to any disclaimer, the term of this patent is extended or adjusted under 35 U.S.C. 154(b) by 543 days.

(21) Appl. No.: 15/327,535

(22) PCT Filed: Dec. 3, 2015

(86) PCT No.: PCT/IN2015/000442
§ 371 (c)(1),
(2) Date: Jan. 19, 2017

(87) PCT Pub. No.: WO2016/092558
PCT Pub. Date: Jun. 16, 2016

(65) Prior Publication Data
US 2017/0202524 A1  Jul. 20, 2017

(30) Foreign Application Priority Data

Dec. 11, 2014  (IN) .......................... 3652/DEL/2014

(51) Int. Cl.
*A61B 6/04* (2006.01)
*A61B 6/00* (2006.01)
*A61B 6/03* (2006.01)
*A61B 90/00* (2016.01)
*A61B 6/12* (2006.01)
*A61N 5/10* (2006.01)

(52) U.S. Cl.
CPC ............ *A61B 6/0492* (2013.01); *A61B 6/032* (2013.01); *A61B 6/12* (2013.01); *A61B 6/501* (2013.01); *A61B 6/52* (2013.01); *A61B 90/39* (2016.02); *A61B 2090/3966* (2016.02); *A61B 2090/3991* (2016.02); *A61N 5/1049* (2013.01); *A61N 2005/1061* (2013.01)

(58) Field of Classification Search
CPC ......... A61B 6/0492; A61B 6/501; A61B 6/12; A61B 6/52; A61B 6/032; A61B 90/39; A61B 2090/3991; A61B 2090/3966; A61N 2005/1061; A61N 5/1049
See application file for complete search history.

(56) References Cited

U.S. PATENT DOCUMENTS

| | | |
|---|---|---|
| 5,052,035 A | 9/1991 | Krupnick |
| 5,799,059 A | 8/1998 | Stembridge et al. |
| 2015/0223906 A1 | 8/2015 | O'Neill et al. |

FOREIGN PATENT DOCUMENTS

| | | |
|---|---|---|
| WO | 2014009967 A1 | 1/2014 |
| WO | 2014032171 A1 | 3/2014 |

*Primary Examiner* — Mark Bockelman
(74) *Attorney, Agent, or Firm* — The Webb Law Firm

(57) ABSTRACT

This invention relates to a device for identifying the location of internal anatomical features by externally marking on skin during a CAT scan comprising a flexible sheet having a plurality of intersecting lines mounted with at least one 3D structure wherein the sheet is provided in the form of a mesh comprising an x-ray opaque material.

8 Claims, 2 Drawing Sheets

DEVICE FOR EXTERNALLY MARKING THE LOCATION OF ORGANS ON SKIN DURING A CAT SCAN

CROSS-REFERENCE TO RELATED APPLICATIONS

This application is the United States national phase of International Application No. PCT/IN2015/000442 filed Dec. 3, 2015, and claims priority to Indian Patent Application No. 3652/DEL/2014 filed Dec. 11, 2014, the disclosures of which are hereby incorporated in their entirety by reference.

FIELD OF INVENTION

This invention relates to an improved device for externally marking the location of organs on skin during a CAT scan.

BACKGROUND/PRIOR ART OF INVENTION

In today's medical world Computerized Tomography scanning (a CT or CAT scan) is known to be very common investigation procedure, which provides a cross sectional view of the body. CAT scans are used to locate organs and anatomical features or abnormalities such as lesions and tumors within the organs Conventional X-ray generates only two dimensional flat view of organs. However, use of a CAT scan provides for viewing of organs in three dimensional form as well.

For planning a medical procedure such as surgical operation or radiation therapy, identifying the location of anatomical features such as organs, defects, lesions or tumors by reference to a location on the surface of the body (skin) is very important.

There are several methods for marking the location of organs externally on skin. The oldest and most common method involves identifying body landmarks from which the distance to organs is calculated, followed by marking the location. However such method has its own possibility of errors.

Another method involves the use of radio-opaque markings on skin followed by CAT scan. However, it may need multiple scan to delineate an organ with the possibilities of errors. This is because the exact position of the organ cannot be located accurately just by placing the marker randomly. Thus, there are fair chances of involvement of the errors.

Another method involves carrying out the CAT scan with sheets comprising of oblique radio-opaque lines. In this method, the resultant image must be processed through a special computer program and translated on to specialized equipment called stereo-tactic device. Thus, the drawback associated with this method include that it requires special computer program and stereo-tactic frame (equipment), which is very expensive and requires special training.

Hence, there is a need to develop a novel device for marking location of organs on skin as per CAT scan to assist medical persons, which can address the aforesaid problems. In particular, such devices should not require the use of expensive specialized equipment so that it is more readily available. The device and method should also result in accurate and reproducible CAT scans. With the help of this device a medical person can easily mark on skin location of organs as per CAT scan.

OBJECTS OF THE INVENTION

The primary object of the present invention is to provide an improved device for externally marking the location of organs on skin during a CAT scan.

Another object of the present invention is to provide an improved device for externally marking the location of organs on skin during a CAT scan which is efficient and reliable.

Still another object of the present invention is to provide an improved device for externally marking the location of organs on skin during a CAT scan which facilitates identification of level of section in CT scan.

SUMMARY OF THE INVENTION

According to this invention, there is provided an improved device for marking on skin the location of organs and anatomical features identified in a CAT scan. The device is a flexible sheet having a plurality of lines wherein the sheet comprises an x-ray opaque material, for example barium sulphate, and is provided in the form of a mesh. The sheet can be made of soft bendable plastic such as low density polyethylene. The lines can be a series of vertical and horizontal lines. The vertical lines may be thicker than the horizontal lines. The vertical lines can be arranged in a pattern of thick and thin lines at regular intervals, for example every fifth vertical line can be thicker than the intervening vertical lines. The x-ray opaque material may be impregnated within or coated on the flexible sheet.

This invention also discloses another type of craniomapper, which is called craniomapper coronal. This is used for obtaining coronal section. So that, location of lesions in vertex area can be marked.

The invention is also a method of identifying the location of an internal anatomical feature during a CAT scan comprising placing the flexible sheet on a surface of the body, performing the CAT scan; identifying the internal anatomical feature to be located; and identifying the location of the anatomical feature by reference to the position on the flexible sheet.

The anatomical feature can be, for example, an organ, a defect, a lesion or a tumor. The surface of the body to which the sheet is applied can be the head.

The invention thus provides a device for marking location of organs on skin as per CAT scan which is simple to use by common medical persons.

The invention has the advantage of marking location of organs on skin as per CAT scan which is cost effective. In addition, the device is easy to use and convenient to manufacture.

STATEMENT OF INVENTION

According to this invention, there is provided an improved device for identifying the location of internal anatomical features by externally marking on skin during a CAT scan comprising a flexible sheet having a plurality of intersecting lines mounted with atleast one structure wherein the sheet is provided in the form of a mesh comprising an x-ray opaque material.

BRIEF DESCRIPTION OF THE ACCOMPANYING DRAWINGS

Further objects and advantages of this invention will be more apparent from the ensuing description when read in conjunction with the accompanying drawings indicating exemplary embodiments of the present invention and wherein.

DETAIL DESCRIPTION OF THE INVENTION WITH REFERENCE TO THE ACCOMPANYING DRAWINGS

Figure 1:
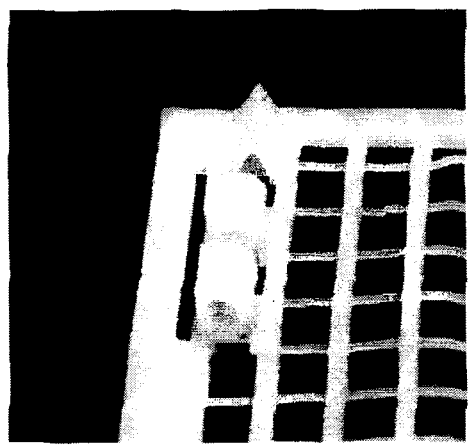
FIG. 1 shows: Top view of device according to an embodiment of the invention.

The invention is directed to a device for marking location of organs on skin used with a CAT scan. In exemplary embodiments, the device can be used for CAT scans of the head, for example for use in for neurosurgery. As shown in FIG. 1, the device is made of flexible material, such as a plastic, although other suitable materials readily apparent to persons skilled in the art may be used. The flexible material is impregnatedor coated with a x-ray opaque material such as Barium Sulphate, Bismuth Subcarbonate, Bismuth oxychloride, Zirconium oxide, wherein Barium Sulphate is most commonly used material. The invention is not restricted to the use of examples given and other x-ray opaque materials used in the art are understood to be within the scope of the invention. An exemplary flexible material is any bendable or soft plastic such as Low Density Polyehtylene. In an exemplary method of making the inventive device x-ray opaque heavy metal substance, such as Barium Sulphate, can be impregnated into the flexible material by mixing with the plastic prior to molding in order to impart radio-opacity. In other embodiments, the x-ray opaque material is coated onto the flexible material after molding.

In one embodiment, the device provides a mesh that creates a plurality of horizontal lines and vertical lines. According to an exemplary embodiment, the horizontal lines are evenly spaced and relatively thin.

Figure 2:
FIG. 2 illustrates: Exemplary embodiment of 3D structure employed in the present invention.
Figure 3:
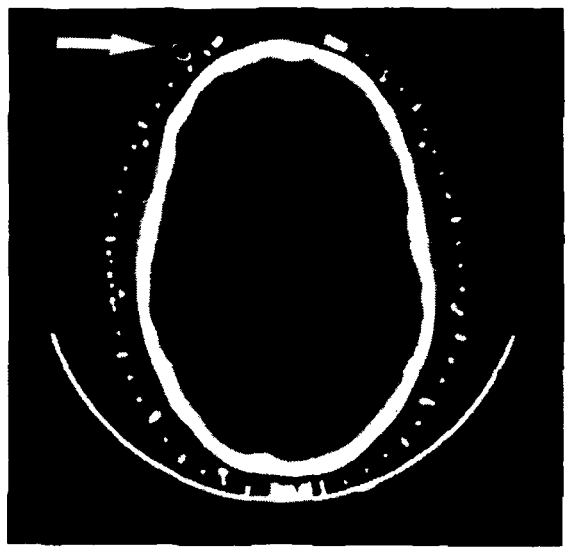
FIG. 3-5 shows: CAT scan image utilizing the present invention.
Figure 4:
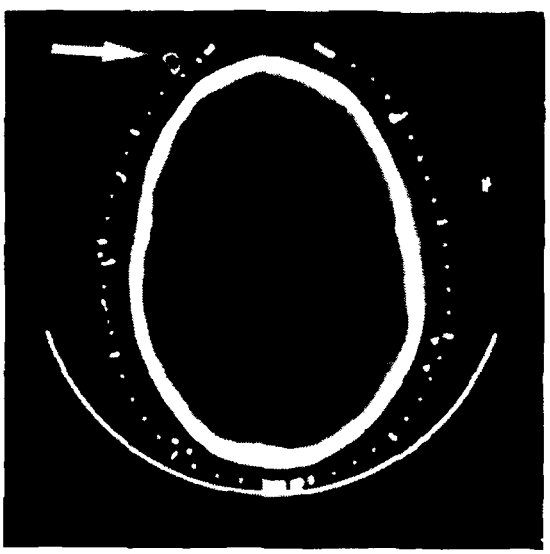
Figure 5:
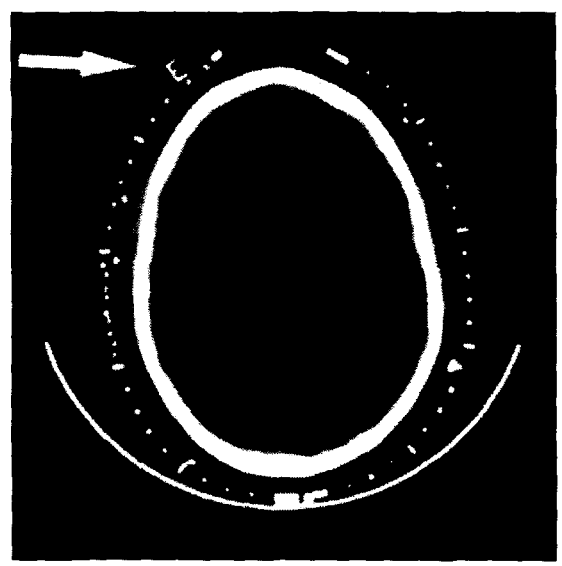

The vertical lines are also evenly spaced and are thicker than the horizontal lines. To improve the ability to define reference points in the scans resulting from use of the device, thicker vertical lines can be created in regular intervals. For example, in the exemplary embodiment shown in FIG. 1, every fifth vertical line is thicker than intervening four lines. For example, the vertical lines can be spaced at 1 cm intervals and the thicker lines spaced at five cm intervals. In order to indicate vertical level of horizontal cross section in CAT scan, a plurality of 3D structure such as Alphabets can be employed as in FIG. 2. These letters are permanently placed on the mapping device. In CAT scan image, these are visible easily as letters i.e. in exact shape as illustrated in FIG. 3-5. The 3D structure is preferably made of radio opaque material and can take any shape without restricting to alphabets.

It can be observed from the FIG. 3-5, it is very easy and convenient to locate the vertical level of horizontal cross section (Cut section) of CAT scan without requiring the user to strain his brain to find the same.

Thus, instead of diagonal lines any 3D structure can be used in the present invention to designate vertical level of section in CAT scan.

As also shown in FIG. 1, the device can be rectangular with band. However, other shapes such as circular or elliptical can be used. Various shapes may be used for application to different parts of the body. As illustrated, the device is essentially flat. However, the invention is not limited to such a flat device and can be molded in any suitable shape depending on use and application.

In use, the device is applied externally to the location of body where the CAT scan will be obtained, for example around a head, before taking the CAT scan. Marking accuracy of this device is in the range of +/−5 mm.

A CAT scan taken while utilizing the device according to the invention is illustrated in FIG. 3-5.

As can be seen, the identifying and marking of a location is apparent and very easy. The position of the 3D structure indicates vertical position in CAT scan and vertical lines show horizontal position. Crossing of these two positions reflects exact location of organ/point of interest/lesion. The horizontal lines are meant to hold vertical lines in place.

For procedures such as surgical & radiotherapy, localizing and marking location of different lesions/organs on skin is very important. CAT scan gives rise to a sectional view of organs, but it is difficult to mark location of lesions/organs on skin after CAT scan. However, the present invention facilitates accurately localizing and marking the organs visible in CAT Scan.

Device of the instant invention is made of a radio-opaque grid of vertical lines. This grid is visible in CAT scan as dots in a circular manner around the head. The dots are small for each 1 cm and bigger for each 5 cm distance. Further, there is appearance of exact shape of 3D structure adjacent to the circle of dots. This shows vertical position.

Instructions for Application of Device
1. Apply the device around the head.
2. Thread hook & loop fastener (or other suitable fastener) through the hole.
3. Lightly tighten it and press against itself to lock it.
4. On the front side it should be at the level of lower ridge of frontal bone.
5. In the middle it should rest on the ear lobule.
6. To correlate precisely position of device may be marked on skin.
7. Frontal and side marking.

The above describes craniomapper transverse which is used for transverse section of skull, wherein top of skull is not well defined. Only front, back and sides of skull are covered. Lesions present in vertex area of skull are not visible clearly in the transverse CR scan. To visualize this area, coronal section is required. Therefore, another type of craniomapper is provided, which is called craniomapper coronal. This is used for marking location of lesions in vertex area.

Said craniomapper coronal is also made of radio-opaque grid. The craniomapper coronal is same as craniomapper transverse in terms of construction.

In said craniomapper coronal, top of skull and sides are well defined, wherein the slices are cut by CT scan parallel to face.

Instructions of Application of Craniomapper Coronal
Apply the craniomapper on the head covering top and sides of head.
Snap join back head band.
Thread hook and loop fastener through the buckle and fastener
Join shape band on the front and back side to maintain shape of craniomapper.
On the front side, measure the height of sides of craniomapper from tip of nose with a special scale.
Make sure to keep position of craniomapper from lobule of ear identical on both sides of head.
To correlate precisely, position of craniomapper may be marked on side.

Application

For radiotherapy of head, the point of radiotherapy is localized.

For other parts of body: Localization/marking of organs on skin after CAT scan. For ex: fixing the device on chest to mark and localize lung tumors on skin. Here, the device is fixed on body by means of adhesive tapes. Its position is marked on skin with a marker. So that, correlation can be done after CAT Scan.

For surgery of Brain to localize tumors:

The device helps in exact localization of pathology during surgery.

It is to be noted that the present invention is susceptible to modifications, adaptations and changes by those skilled in the art. Such variant embodiments employing the concepts and features of this invention are intended to be within the scope of the present invention, which is further set forth under the claims that follow.

I claim:

1. A device for identifying the location of internal anatomical features by externally marking on skin during a CAT scan comprising a flexible sheet having a plurality of intersecting lines with at least one 3D structure mounted on the sheet, wherein the sheet is a mesh comprising an x-ray opaque material, and wherein the at least one 3D structure is at least one alphabet letter oriented at an angle to the sheet sufficiently so that the alphabet letter is recognizable when viewing in a direction generally parallel to the sheet surface.

2. The device according to claim 1, wherein said plurality of intersecting lines comprise at least one vertical line and at least one horizontal line.

3. The device according to claim 1, wherein the at least one vertical line is thicker than the at least one horizontal line.

4. The device according to claim 2, wherein the at least one vertical line is arranged in a pattern of thick and thin lines.

5. The device according to claim 2, wherein every fifth vertical line of the at least one vertical line is thicker than the intervening vertical lines.

6. The device according to claim 1, wherein the structure comprises 3D structure visible in a CAT scan image.

7. The device according to claim 1, wherein the 3D structure indicates a vertical position in the CAT scan and the at least one vertical line reflects a horizontal position, in which crossing of said horizontal position and said vertical position depicts the location of the internal anatomical features.

8. The device according to claim 1, wherein the flexible sheet lacks any oblique lines.

* * * * *